US011937930B2

(12) United States Patent
Salti et al.

(10) Patent No.: US 11,937,930 B2
(45) Date of Patent: Mar. 26, 2024

(54) COGNITIVE STATE-BASED SEAMLESS STIMULI

(71) Applicant: ADAM COGTECH LTD., Beit Yehoshua (IL)

(72) Inventors: Moti Salti, Kiryat Ono (IL); Lidror Troyansky, Givataim (IL); Erez Aluf, Beit Yehoshua (IL)

(73) Assignee: ADAM COGTEC LTD., Beit Yehoshua (IL)

( * ) Notice: Subject to any disclaimer, the term of this patent is extended or adjusted under 35 U.S.C. 154(b) by 122 days.

(21) Appl. No.: 17/032,979

(22) Filed: Sep. 25, 2020

(65) Prior Publication Data

US 2021/0077006 A1 Mar. 18, 2021

Related U.S. Application Data

(63) Continuation of application No. PCT/IL2019/050357, filed on Mar. 28, 2019.

(60) Provisional application No. 62/649,552, filed on Mar. 28, 2018.

(51) Int. Cl.
*G08B 23/00* (2006.01)
*A61B 5/00* (2006.01)
(Continued)

(52) U.S. Cl.
CPC .............. *A61B 5/18* (2013.01); *A61B 5/01* (2013.01); *A61B 5/1112* (2013.01);
(Continued)

(58) Field of Classification Search
CPC ......... A61B 5/18; A61B 5/1171; A61B 5/163; A61B 5/01; A61B 5/1112; A61B 5/7275
(Continued)

(56) References Cited

U.S. PATENT DOCUMENTS

2008/0236929 A1* 10/2008 Fukaya ............... B60T 7/22
707/999.107
2011/0149064 A1* 6/2011 Uehira ............... H04N 7/183
348/744
(Continued)

FOREIGN PATENT DOCUMENTS

DE 102015210782 A1 12/2016
JP 2008-120271 A 5/2008
JP 2008120271 A 5/2008

OTHER PUBLICATIONS

The extended European search report with the supplementary European search report and the European search opinion, issued by the European Patent Office for corresponding European Patent Application No. 19777694.1-1122, dated Oct. 19, 2021.
(Continued)

*Primary Examiner* — Naomi J Small
(74) *Attorney, Agent, or Firm* — Myers Wolin, LLC

(57) ABSTRACT

Method, apparatus and product for providing cognitive state-based seamless stimuli. The method comprising: obtaining a cognitive state of a human subject; determining a target cognitive state for the human subject; determining, based on the cognitive state and the target cognitive state, a saliency level for a stimuli, wherein the saliency level is configured to cause the human subject to direct spatial attention to the stimuli, wherein the saliency level is configured to cause the stimuli to be seamless for the human subject given the cognitive state; and outputting the stimuli at the saliency level to be perceived by the human subject.

23 Claims, 5 Drawing Sheets

(51) Int. Cl.
   *A61B 5/01* (2006.01)
   *A61B 5/11* (2006.01)
   *A61B 5/1171* (2016.01)
   *A61B 5/16* (2006.01)
   *A61B 5/18* (2006.01)
(52) U.S. Cl.
   CPC ............ *A61B 5/1171* (2016.02); *A61B 5/163* (2017.08); *A61B 5/7275* (2013.01)
(58) Field of Classification Search
   USPC ........................................................ 340/576
   See application file for complete search history.

(56) References Cited

U.S. PATENT DOCUMENTS

| | | | |
|---|---|---|---|
| 2012/0212353 A1 | 8/2012 | Fung et al. | |
| 2013/0124076 A1* | 5/2013 | Bruni | G08G 5/0091 701/120 |
| 2014/0139341 A1* | 5/2014 | Green | A61B 5/163 340/576 |
| 2016/0117947 A1* | 4/2016 | Misu | B60W 50/085 434/62 |
| 2016/0196105 A1* | 7/2016 | Vartakavi | G06F 16/639 700/94 |
| 2017/0308770 A1* | 10/2017 | Jetley | G06V 10/462 |
| 2019/0143989 A1* | 5/2019 | Oba | B60W 40/08 701/70 |
| 2021/0182604 A1* | 6/2021 | Anthony | B60W 30/00 |

OTHER PUBLICATIONS

International Search Report issued for corresponding International Patent Application No. PCT/IL2019/050357 dated Jul. 9, 2019.

* cited by examiner

COGNITIVE STATE-BASED SEAMLESS STIMULI

CROSS-REFERENCE TO RELATED APPLICATION

This application is a continuation of international application No. PCT/IL2019/050357, filed Mar. 28, 2019, and entitled "Cognitive State-Based Seamless Stimuli", which claims the benefit of provisional patent application No. 62/649,552, and entitled SYSTEM AND METHOD FOR OPTIMIZING DRIVER ENGAGEMENT, filed Mar. 28, 2018, which are hereby incorporated by reference in its entirety without giving rise to disavowment.

TECHNICAL FIELD

The present disclosure relates to stimuli and alerts in general, and to seamless stimuli that depends on a cognitive state of the subject thereof, in particular.

BACKGROUND

Partly-autonomous vehicles become prevalent during the last years, and it is foreseeable that their number would increase incrementally in the next years.

Attempts to apply such hybrid systems, in which vehicle control is divided by human driver and autonomous machine have gained, so far, very limited success. It seems that a beneficial balance between these two entities is very hard to gain. On the one hand, some of the human drivers seem to have over confidence in the machine and are not receptive at all to a call to take over, while others were anxious with machine taking control and did not benefit from the autonomous driving.

Previous attempts to mitigate these challenges focus mainly on constructing fully autonomous vehicles or better alert systems. However, the need for minimizing false negatives in such systems usually results on a higher rates of false positives and requests to intervene.

BRIEF SUMMARY

One exemplary embodiment of the disclosed subject matter is a method comprising: obtaining a cognitive state of a human subject; determining a target cognitive state for the human subject; determining, based on the cognitive state and the target cognitive state, a saliency level for a stimuli, wherein the saliency level is configured to cause the human subject to direct spatial attention to the stimuli, wherein the saliency level is configured to cause the stimuli to be seamless for the human subject given the cognitive state; and outputting the stimuli at the saliency level to be perceived by the human subject.

Optionally, the human subject is a driver of a partly-autonomous vehicle.

Optionally, the target cognitive state is associated with a hazard facing the partly-autonomous vehicle.

Optionally, said determining the saliency level is performed based on a model, wherein the model is updated based on identified responses of the driver to a plurality of stimuli.

Optionally, said determining the saliency level is performed based on the cognitive state of the driver, an assessed risk level and an assessed urgency level.

Optionally, the stimuli is supraliminal and above a conscious perception level for the human subject.

Optionally, the stimuli is a visual stimuli presented to be perceived by peripheral vision of the human subject.

Optionally, the target cognitive state comprises a spatial attention in a direction of an object, wherein the stimuli is associated with a location of the object.

Optionally, the stimuli is a visual stimuli that is presented in a relative location in a field of view of the human subject that is in proximity to the object, with respect to the field of view.

Optionally, the stimuli is an audio stimuli that is configured to be perceived by the human subject with an associated relative location, wherein the relative location is relative to the human subject and corresponds the location of the object.

Optionally, the stimuli is a visual stimuli, wherein the saliency level is at least one of the following: a size of the visual stimuli, an opacity level of the visual stimuli, a brightness level of the visual stimuli, and a duration in which the visual stimuli is presented.

Optionally, the stimuli is an audio stimuli, wherein the saliency level is at least one of the following: a volume level of the audio stimuli, a frequency spectrum of the audio stimuli, a similarity measurement of the audio stimuli with respect to a background noise, and a duration in which the audio stimuli is provided.

Optionally, the target cognitive state minimizes a following function: $f(c)=\alpha \cdot \text{Risk}(c) - \beta \cdot \text{WellBeing}(c)$, wherein c is a cognitive state, wherein $\text{Risk}(c)$ is a function of a risk depending on the cognitive state, wherein $\text{WellBeing}(c)$ is a function of a well being of the human subject given the cognitive state, wherein $\alpha$ and $\beta$ are coefficients.

Optionally, $\text{Risk}(c)$ is a function of an expected damage that is defined as $\text{Risk}(c)=\text{Damage} \cdot \text{Probability}(c)$, where Damage is an expected damage from a hazard, wherein $\text{Probability}(c)$ is a function of a probability that the damage will occur, given the cognitive state of the human subject.

Optionally, said determining the saliency level is based on a wellbeing of the human subject, wherein the wellbeing of the human subject is assessed using at least one of the following: a facial expression of the human subject; eye saccades of the human subject; one or more body gestures of the human subject; and one or more changes in body temperature of the human subject.

Optionally, said determining a saliency level for a stimuli is performed using a predictive model, wherein the predictive model is configured to estimate an estimated saliency level for a stimuli so as to provide a seamless stimuli while directing spatial attention to the stimuli, wherein the predictive model provides the estimated saliency level based on the cognitive state, the target cognitive state and a characteristic of the human subject.

Optionally, the predictive model is trained based on crowd-sourced information relating to different people driving different vehicles.

Optionally, said determining the saliency level is performed based on a predictive model; wherein the method further comprising: identifying response of the human subject to the stimuli; and updating the predictive model, whereby improving determination of saliency levels in future usages of the predictive model.

Optionally, said identifying the response comprises obtaining a new cognitive state of the human subject, wherein said updating the predictive model is based on a difference between the new cognitive state and the target cognitive state.

Optionally, the response is indicative that the stimuli was not seamless to the human subject, and wherein said updating the predictive model comprises updating the model to provide a lower saliency level than the saliency level determined in said determining the saliency level for a same condition.

Optionally, the response is indicative that the stimuli did not cause the human subject to direct spatial attention to the stimuli, and wherein said updating the predictive model comprises updating the model to provider a higher saliency level than the saliency level determined in said determining the saliency level for a same condition.

Another exemplary embodiment of the disclosed subject matter is an apparatus comprising a processor and coupled memory, the processor being adapted to perform: obtaining a cognitive state of a human subject; determining a target cognitive state for the human subject; determining, based on the cognitive state and the target cognitive state, a saliency level for a stimuli, wherein the saliency level is configured to cause the human subject to direct spatial attention to the stimuli, wherein the saliency level is configured to cause the stimuli to be seamless for the human subject given the cognitive state; and outputting the stimuli at the saliency level to be perceived by the human subject.

Optionally, said apparatus is integrated in a partly-autonomous vehicle, wherein the human subject is a driver of the partly-autonomous vehicle.

Optionally, the target cognitive state is associated with a hazard facing the partly-autonomous vehicle.

Optionally, said determining the saliency level is performed based on a model, wherein the model is updated based on identified responses of the driver to a plurality of stimuli.

Optionally, said determining the saliency level is performed based on the cognitive state of the driver, an assessed risk level and an assessed urgency level.

Optionally, the stimuli is a visual stimuli presented to be perceived by peripheral vision of the human subject.

Optionally, the target cognitive state comprises a spatial attention in a direction of an object, wherein the stimuli is associated with a location of the object.

Optionally, the stimuli is a visual stimuli that is presented in a relative location in a field of view of the human subject that is in proximity to the object, with respect to the field of view.

Optionally, the stimuli is an audio stimuli that is configured to be perceived by the human subject with an associated relative location, wherein the relative location is relative to the human subject and corresponds the location of the object.

Optionally, the stimuli is a visual stimuli, wherein the saliency level is at least one of the following: a size of the visual stimuli, an opacity level of the visual stimuli, a brightness level of the visual stimuli, and a duration in which the visual stimuli is presented.

Optionally, the stimuli is an audio stimuli, wherein the saliency level is at least one of the following: a volume level of the audio stimuli, a frequency spectrum of the audio stimuli, a similarity measurement of the audio stimuli with respect to a background noise, and a duration in which the audio stimuli is provided.

Optionally, the target cognitive state minimizes a following function: $f(c) = \alpha \cdot Risk(c) - \beta \cdot WellBeing(c)$, wherein c is a cognitive state, wherein $Risk(c)$ is a function of a risk depending on the cognitive state, wherein $WellBeing(c)$ is a function of a well being of the human subject given the cognitive state, wherein $\alpha$ and $\beta$ are coefficients.

Optionally, said determining the saliency level is based on a wellbeing of the human subject, wherein the wellbeing of the human subject is assessed using at least one of the following: a facial expression of the human subject; eye saccades of the human subject; one or more body gestures of the human subject; and one or more changes in body temperature of the human subject.

Optionally, said determining a saliency level for a stimuli is performed using a predictive model, wherein the predictive model is configured to estimate an estimated saliency level for a stimuli so as to provide a seamless stimuli while directing spatial attention to the stimuli, wherein the predictive model provides the estimated saliency level based on the cognitive state, the target cognitive state and a characteristic of the human subject.

Optionally, the predictive model is trained based on crowd-sourced information relating to different people driving different vehicles.

Optionally, said determining the saliency level is performed based on a predictive model; wherein said processor is configured to perform: identifying response of the human subject to the stimuli; and updating the predictive model, whereby improving determination of saliency levels in future usages of the predictive model.

Optionally, said identifying the response comprises obtaining a new cognitive state of the human subject, wherein said updating the predictive model is based on a difference between the new cognitive state and the target cognitive state.

Optionally, the response is indicative that the stimuli was not seamless to the human subject, and wherein said updating the predictive model comprises updating the model to provide a lower saliency level than the saliency level determined in said determining the saliency level for a same condition.

Optionally, the response is indicative that the stimuli did not cause the human subject to direct spatial attention to the stimuli, and wherein said updating the predictive model comprises updating the model to provider a higher saliency level than the saliency level determined in said determining the saliency level for a same condition.

Yet another exemplary embodiment of the disclosed subject matter is a non-transitory computer readable medium retaining program instructions, which program instructions when read by a processor, cause the processor to perform: obtaining a cognitive state of a human subject; determining a target cognitive state for the human subject; determining, based on the cognitive state and the target cognitive state, a saliency level for a stimuli, wherein the saliency level is configured to cause the human subject to direct spatial attention to the stimuli, wherein the saliency level is configured to cause the stimuli to be seamless for the human subject given the cognitive state; and outputting the stimuli at the saliency level to be perceived by the human subject.

Optionally, said non-transitory computer readable medium is loaded, at least partially, in a memory unit of a partly-autonomous vehicle, wherein the human subject is a driver of the partly-autonomous vehicle.

Optionally, the target cognitive state is associated with a hazard facing the partly-autonomous vehicle.

Optionally, said determining the saliency level is performed based on a model, wherein the model is updated based on identified responses of the driver to a plurality of stimuli.

Optionally, said determining the saliency level is performed based on the cognitive state of the driver, an assessed risk level and an assessed urgency level.

Optionally, the stimuli is a visual stimuli presented to be perceived by peripheral vision of the human subject.

Optionally, the target cognitive state comprises a spatial attention in a direction of an object, wherein the stimuli is associated with a location of the object.

Optionally, the stimuli is a visual stimuli that is presented in a relative location in a field of view of the human subject that is in proximity to the object, with respect to the field of view.

Optionally, the stimuli is an audio stimuli that is configured to be perceived by the human subject with an associated relative location, wherein the relative location is relative to the human subject and corresponds the location of the object.

Optionally, the stimuli is a visual stimuli, wherein the saliency level is at least one of the following: a size of the visual stimuli, an opacity level of the visual stimuli, a brightness level of the visual stimuli, and a duration in which the visual stimuli is presented.

Optionally, the stimuli is an audio stimuli, wherein the saliency level is at least one of the following: a volume level of the audio stimuli, a frequency spectrum of the audio stimuli, a similarity measurement of the audio stimuli with respect to a background noise, and a duration in which the audio stimuli is provided.

Optionally, the target cognitive state minimizes a following function: $f(c) = \alpha \cdot Risk(c) - \beta \cdot WellBeing(c)$, wherein c is a cognitive state, wherein Risk(c) is a function of a risk depending on the cognitive state, wherein WellBeing(c) is a function of a well being of the human subject given the cognitive state, wherein $\alpha$ and $\beta$ are coefficients.

Optionally, said determining the saliency level is based on a wellbeing of the human subject, wherein the wellbeing of the human subject is assessed using at least one of the following: a facial expression of the human subject; eye saccades of the human subject; one or more body gestures of the human subject; and one or more changes in body temperature of the human subject.

Optionally, said determining a saliency level for a stimuli is performed using a predictive model, wherein the predictive model is configured to estimate an estimated saliency level for a stimuli so as to provide a seamless stimuli while directing spatial attention to the stimuli, wherein the predictive model provides the estimated saliency level based on the cognitive state, the target cognitive state and a characteristic of the human subject.

Optionally, the predictive model is trained based on crowd-sourced information relating to different people driving different vehicles.

Optionally, said determining the saliency level is performed based on a predictive model; wherein said program instruction are configured to cause the processor to perform: identifying response of the human subject to the stimuli; and updating the predictive model, whereby improving determination of saliency levels in future usages of the predictive model.

Optionally, said identifying the response comprises obtaining a new cognitive state of the human subject, wherein said updating the predictive model is based on a difference between the new cognitive state and the target cognitive state.

Optionally, the response is indicative that the stimuli was not seamless to the human subject, and wherein said updating the predictive model comprises updating the model to provide a lower saliency level than the saliency level determined in said determining the saliency level for a same condition.

Optionally, the response is indicative that the stimuli did not cause the human subject to direct spatial attention to the stimuli, and wherein said updating the predictive model comprises updating the model to provider a higher saliency level than the saliency level determined in said determining the saliency level for a same condition.

THE BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

Figure 1:
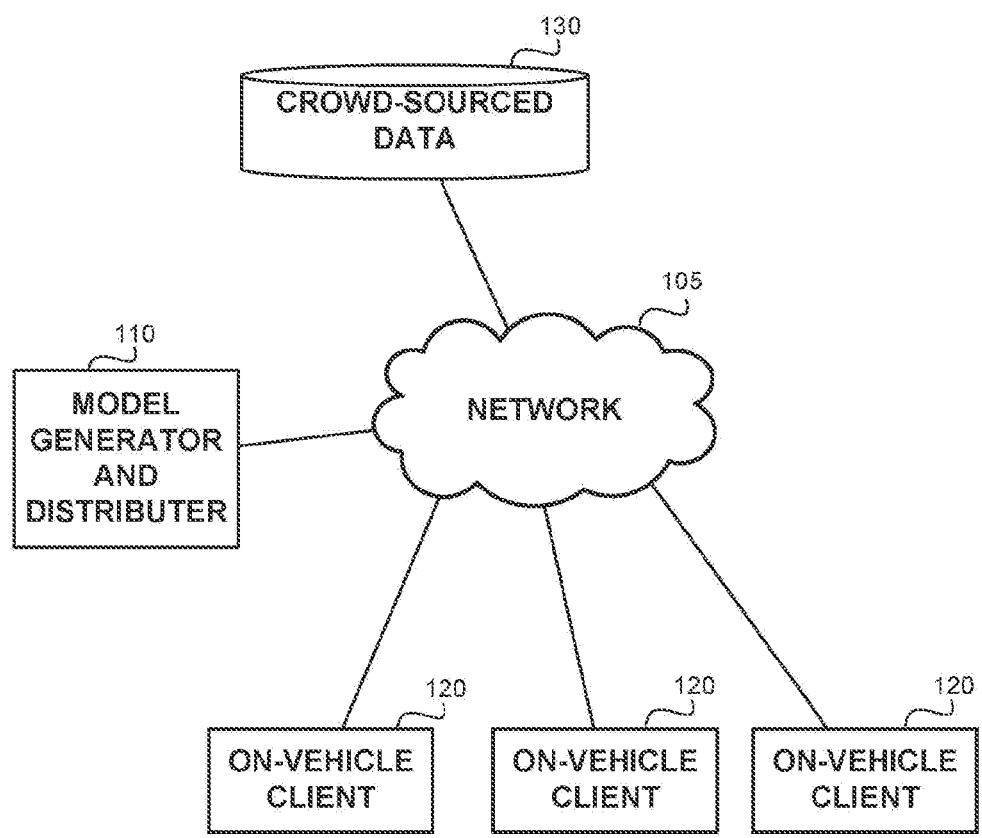
FIG. 1 shows an illustration of an environment, in accordance with some exemplary embodiments of the disclosed subject matter.

One technical problem dealt with by the disclosed subject matter is to provide a system and a method for managing a human subject's attention. In particular, the technical problem may be applicable to the field of driving a partly-autonomous vehicle. However, such embodiment is merely an example, and the disclosed subject matter is not limited to such field, and may be used for other human subjects and in other scenarios.

It may be desired to be able to manage the driver's receptivity and engagement. In some cases, it is desired to provide stimuli to modify the driver's cognitive state to a target cognitive state.

Another technical problem may be to provide a seamless stimuli to the driver that would still be useful to modify the driver's cognitive state. The seamless stimuli may be a stimuli that is a supraliminal stimuli, which is above a conscious perception level of the driver, and not a subliminal stimuli. In some cases, given the cognitive resources available to the driver, the stimuli may be undetectable to the human driver. As an example, the cognitive state of the driver may include cognitive engagement, utilizing the cognitive resources of the driver, and causing an inattentional blindness. However, the disclosed subject matter is not limited to seamless stimuli resulting from inattentional blindness, and other cognitive mechanisms may cause a supraliminal stimuli to be perceived as a seamless stimuli.

In some exemplary embodiments, the same supraliminal stimuli may be seamless to one driver and not seamless to another. Additionally or alternatively, the same supraliminal stimuli may be seamless and not seamless to the same driver, at different cognitive states. It may be desired to determine which stimuli to apply in order for the stimuli to be perceived as a seamless stimuli by the driver at the present situation thereof.

In some cases, the seamless stimuli may be configured to cause spatial attention to be directed at an object. The object may be, for example, a pedestrian crossing the road and being visible to the driver. In such a case, spatial attention may be directed towards a portion of the windshield. As another example, the object may be a speeding car driving above the speed limit, and being located behind the vehicle of the driver, and being visible via a mirror of the vehicle. In such a case, spatial attention may be directed towards the mirror.

Spatial attention may be part of a cognitive state of a human subject. In some exemplary embodiments, when the human subject addresses cognitive resources to process an area, it may be said that the human subject directs spatial attention to the area. In some cases, spatial attention allows humans to selectively process visual information through prioritization of an area within the visual field. A region of space within the visual field may be selected for attention and the information within this region then receives further processing. In some cases, when spatial attention is evoked, an observer may be typically faster and more accurate at detecting a target that appears in an expected location compared to an unexpected location.

In some cases, cognitive engagement may be the coupling of spatial attention to a specific object over a timeframe. In some cases, when the driver of a partly-autonomous vehicle is performing other non-driving related tasks, the driver may be performing cognitive engagement, reducing his available cognitive resources. The driver's cognitive receptivity may indicate the driver's total available cognitive resources. The receptivity may be affected by internal causes, such as mind wandering, tiredness, consumption of drugs, or the like. The receptivity may be affected by cognitive engagement of the human subject, as such engagement reduces available cognitive resources for other purposes.

One technical solution provided by the disclosed subject matter is to determine a saliency level for a stimuli. The saliency level may be determined based on the cognitive state of the human subject, such as the driver. The saliency level may be determined based on a desired target cognitive state for the driver. It may be desired to change the cognitive state of the driver from his given cognitive state to the target cognitive state. In some cases, the target cognitive state may be associated with a hazard, such as a static hazard facing the partly-autonomous vehicle which always faces vehicles at the location, a dynamic hazard facing the vehicle, or the like.

In some cases, a model may be used to determine the saliency level of the stimuli. The model may be a predictive model defined using deep learning techniques, using Convolutional neural network (CNN), Recurrent Neural Network (RNN), using supervised learning, using Support Vector Machines (SVM), using linear regression, using decision trees, or the like. In some cases, the model may be determined using reinforcement learning. Additionally or alternatively, the model may be determined based on responses of the driver. Additionally or alternatively, the model may be determined based on crowd-sourced responses of drivers, and may be utilized to reflect predicted required saliency level of the stimuli that is estimated to be seamless for a driver having specific characteristics of the given driver.

In some exemplary embodiments, the saliency of the stimuli may be manipulated using one or more factors. For example, in a visual stimuli, the saliency of the stimuli may be controlled by the size of the stimuli, the opacity level of the stimuli, the brightness level of the stimuli, the time duration in which the stimuli is made presented visually, or the like. In some cases, the saliency level of the stimuli may be controlled by the location of the stimuli with respect to the subject's field of view. For example, the visual stimuli may be presented in the subject's peripheral field of view, to be perceived by the subject's periphery vision mechanism. In some exemplary embodiments, when the saliency level is relatively high, the stimuli may be presented closer to the center of gaze. For example, as the saliency level is reduced, the angle between the fixation point of the subject's gaze and the stimuli may be reduced. In some exemplary embodiments, the stimuli may be presented in the far peripheral vision (e.g., over about 60 degrees angle) for a first range of saliency levels. For a second range of saliency levels, which is higher than the first range, the stimuli may be presented in the mid peripheral vision (e.g., between about 30 and about 60 degrees angle from the fixation point). For a third range of saliency levels, which is higher than the second range, the stimuli may be presented in the near peripheral vision (e.g., between about 18 and about 30 degrees), and so forth. In some cases, the stimuli, in relatively high saliency levels may be presented in the central view of the subject. Additionally, or alternatively, the relative location may be determined as a function of the saliency level, such as getting closes to the center of gaze as the saliency level increases, in a linear proportion, in a non-linear proportion, or the like.

In some exemplary embodiments, in an audio stimuli, the saliency of the stimuli may be controlled by the volume of the audio stimuli, the frequency spectrum of the audio stimuli, the duration in which the audio stimuli is provided or the like. In some exemplary embodiments, the audio stimuli may be provided in a manner that is similar to that of a background noise. Additionally, or alternatively, a pattern matching the background noise may be used for the audio stimuli. In some exemplary embodiments, as the saliency level decreases, the audio stimuli may be more and more similar to the background noise, being relatively undetectable therefrom.

In some exemplary embodiments, the target cognitive state may be determined by factoring at least two factors: the wellbeing of the subject, on the one hand, and the risk level, on the other hand. For example, the target cognitive state may minimize the following function: $f(c) = \alpha \cdot Risk(c) - \beta \cdot WellBeing(c)$, where c is a cognitive state, $Risk(c)$ is a function of a risk depending on the cognitive state, $WellBeing(c)$ is a function of a wellbeing of the human subject given the cognitive state, and $\alpha$ and $\beta$ are coefficients. In some cases, the disclosed subject matter may avoid creating a distraction, which reduces the wellbeing of the driver, if the distraction does not provide a big of enough reduction in the risk to the vehicle. For example, if the driver is reading an article, getting his attention away from the screen, would be considered a distraction which would only be performed, if the driver's attention is required to provide a significate risk reduction. As another option, a minor distraction, such as provided using a seamless stimuli, may release cognitive resources from non-driving activities (e.g., resources used by cognitive engagement in non-driving activities) in a relatively seamless manner, without the driver noticing the cause of the release of such cognitive resources. The driver's modified cognitive state may be a state that places the driver in a better position to respond to a manifesting risk, such as respond to another vehicle running a red light in front of the partly-autonomous vehicle.

In some exemplary embodiments, the disclosed subject matter may provide a system that comprises sensors, processors, stimulators and display that enable passive monitoring and an active probing of the driver's status, thereby monitors continuously the receptiveness and the engagement level of the driver. Such monitored attributes of the driver may be compared with corresponding target levels. In some exemplary embodiments, the system may comprise a dynamic control module that utilizes a spectrum of stimuli and various types of rewards operable to alter the levels of engagement and receptiveness of the drivers and to train the drivers for adequate responses, thereby promoting a fast and adaptive response.

In accordance with some embodiments of the disclosed subject matter, a system for monitoring and probing driver's attention in real-time may be provided. The system may allow for a gradual call for engagement, supplying the driver with the relevant information for dealing with road hazards, thereby reducing the scope of possible reactions to relevant and adaptive ones. In some exemplary embodiments, the system may be personally tailored to each user taking into account his physical condition in general (e.g. age, acuity of sight etc.), physical condition at a specific time (e.g. fatigue, alertness, mood, destructions etc.) and the dynamics of ongoing attention allocation, or the like. The system may be personally tailored based on data collected regarding the driver. Additionally, or alternatively, the system may be personally tailored based on data collected regarding the driver and other drivers, such as crowd-sourced data. The system may continuously monitor the driver's status and behavior, probe the driver with a potentially tailored set of stimulus. In some exemplary embodiments, control engineering and reinforcement learning may be utilized by the system to provide an optimal set of stimuli to the driver, thereby allowing to elevate the levels of engagement and receptivity to the required levels. In some embodiments, the system may provide for reinforcement teaching of the driver to produce improved responses.

One technical effect of the disclosed subject matter may be to cause a seamless change to the cognitive state of the human subject. As opposed to noticeable stimuli, seamless stimuli may not adversely affect (at least not substantially), the wellbeing of the human subject. In some exemplary embodiments, the seamless stimuli does not interrupt the driver's non-driving activity. Additionally, or alternatively, the seamless stimuli does not irritate the driver.

In some exemplary embodiments, false positive alerts may generally be considered a problem. Systems having high-rate of false positive alerts are generally problematic, as the users learn to ignore such alerts. Low rate of false positive alerts, on the other hand, may be achieved by reducing the sensitivity of the system, but such configuration may also have a corresponding higher rate of false negative, i.e., occasions where the alert should have been issued, but was not. In critical systems, in safety-related system, or the like, false negatives are not generally accepted. Consider a safety system for a vehicle. It is not considered acceptable, that a potential collision would be ignored and not alerted, so as to allow a reduction of false positive alerts (i.e., alerts of collision, where such collision is not likely to occur). The disclosed subject matter may provide an effective solution to this gap. High rate of false positive alerts is substantially meaningless if the alerts are provided in a seamless manner, and they are not actively perceived by the user. The user is not irritated by such false positives, they do not adversely affect his user experience, and he does not and effectively cannot, learn to ignore such alerts.

The disclosed subject matter may provide for one or more technical improvements over any pre-existing technique and any technique that has previously become routine or conventional in the art.

Additional technical problem, solution and effects may be apparent to a person of ordinary skill in the art in view of the present disclosure.

Referring now to FIG. 1 showing an environment, in accordance with some exemplary embodiments of the disclosed subject matter.

On-Vehicle Client 120 may be configured to monitor the cognitive state of the driver, an assessed risk level, an assessed urgency level, or the like. The assessed risk level may reflect a potential risk to the vehicle, such as reflected by static hazards (e.g., vehicle entering a school zone, vehicle reaching a T-junction, or the like), dynamic hazards (e.g., a ball rolling in the road, a pedestrian crossing, or the like), or the like. Static hazards may be obtained based on location data of the vehicle (e.g., obtained from a GPS receiver), and retrieved from navigation systems, third-party servers, or the like. Dynamic hazards may be detected using forward-facing sensors, sensors that are configured to provide measurements external to the vehicle and in the vicinity thereof, data received from other On-Vehicle Clients 120, such as information regarding other vehicles in the vicinity of the vehicle, or the like. The assessed urgency level may be a level of urgency of intervention by the human driver. In some cases, the risk level may be high but the urgency level may be low, as there is sufficient time to respond, if human intervention is required. Additionally, or alternatively, a low risk level may be exhibited with high urgency level, in case the potential of the risk materializing is in fact low, but if the risk materializes the driver must respond immediately.

Additionally or alternatively, On-Vehicle Client 120 may be configured to monitor the driver's cognitive state. The driver's cognitive state may be determined using driver-facing sensors, such as microphone, camera, bio-sensors, or the like.

In some exemplary embodiments, On-Vehicle Client 120 may be configured to determine a target cognitive state based on the current cognitive state of the driver, the assessed risk level, the assessed urgency level, or the like. In some exemplary embodiments, the target cognitive state may be determined using a model that is updated based on identified responses of the driver to a plurality of stimuli. In some cases, the model may be improved over time, to optimize a function that takes into account estimated risk level, estimated required urgency level, wellbeing of the driver, or the like.

In some exemplary embodiments, each On-Vehicle Client 120 may collect data relating to the driver of the vehicle. The data may be used to determine a tailored model to determine target cognitive state to the driver, to determine a model for selecting saliency level with respect to the driver, or the like. In some exemplary embodiments, the data may be transmitted over Network 105 and be stored in a data repository such as Crowd-Sourced Data 130. In some exemplary embodiments, Model Generator and Distributer 110 may collect Crowd-Sourced Data 130 to generate a model based thereof. In some exemplary embodiments, the model may be a predictive model for determining an estimated saliency level for a stimuli so as to provide a seamless stimuli while directing spatial attention to the stimuli. The model may receive, as input, the current cognitive state, the target cognitive state, and a characteristic of the driver. In some exemplary embodiments, the model may be trained based on crowd-sourced information relating to different people, driving different vehicles. In some cases, using Crowd-Sourced Data 130, big data analysis may be enabled to utilize drivers with similar characteristics, such as cognitive patterns, demographic attributes, behavioral attributes, or the like, in order to provide an estimated saliency level for a driver, even in the absence of past information relating thereto. In some cases, the model may be updated based on drivers' responses (or lack thereof), either by the On-Vehicle Client 120 or by Model Generator and Distributer 110. In some exemplary embodiments, Model Generator and Distributer 110 may be configured to distribute the generated or updated model to the On-Vehicle Clients 120, such as periodically, on-demand, on initiation of the client, or the like.

Figure 2:
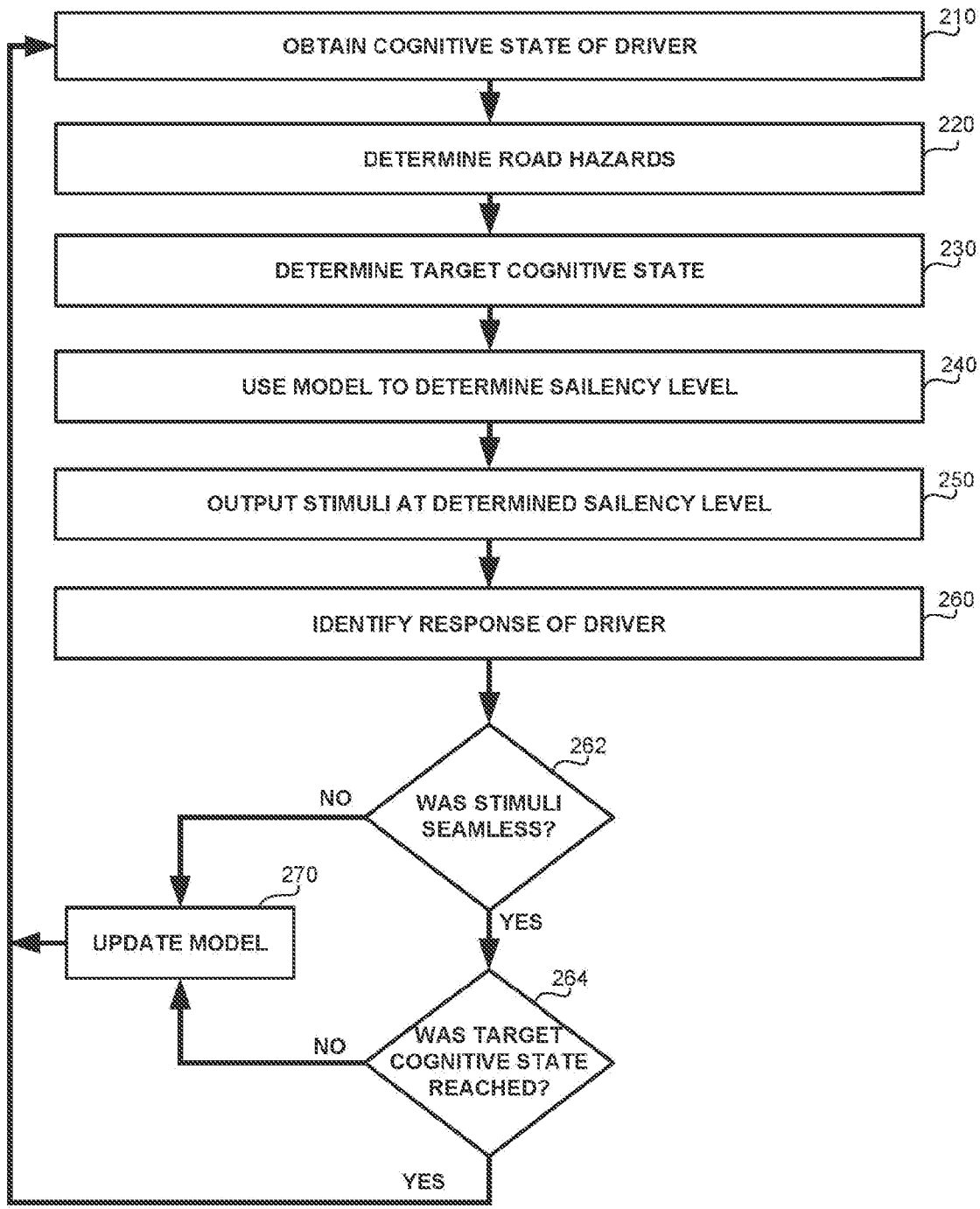
FIG. 2 shows a flowchart diagram of a method, in accordance with some exemplary embodiments of the disclosed subject matter.

Referring now to FIG. 2, showing a flowchart diagram of a method, in accordance with a disclosed subject matter.

On Step 210, a cognitive state of the driver is obtained. The current cognitive state of the driver may be obtained using various sensors, such as but not limited to driver-facing cameras, microphone, eye-tracker, sensors for measuring bio-measurements, or the like. The cognitive state may comprise cognitive receptivity of the driver. Additionally or alternatively, the cognitive state may comprise cognitive attention directed at an object or task. Additionally, or alternatively, the cognitive state may comprise cognitive engagement and duration thereof. Additionally, or alternatively, the cognitive state may comprise cognitive engagement in non-driving activities. Additionally or alternatively, the cognitive state may comprise cognitive engagement in driving activity.

On Step 220, road hazards may be determined. Road hazards may be hazards facing the vehicle driven (at least partially) by the driver. Road hazards may be determined using GPS or positioning module in combination with data from navigation system. Additionally or alternatively, road hazards may be determined based on vehicle-sensors, such as external cameras, microphones, proximity sensors, or the like.

Additionally or alternatively, dynamic hazards may be reported by other connected devices, such as Internet of Things (IoT) devices, connected cars, or the like. For example, another vehicle may report the existence of a hazard in a location that the vehicle is about to reach, such as within about one minute. As a result, a road hazard may be determined for the vehicle.

On Step 230, a target cognitive state may be determined. The target cognitive state may be different than the current cognitive state. The target cognitive state may be determined based on an assessed urgency level, assessed risk level, hazard facing the vehicle, or the like. In some exemplary embodiments, the target cognitive state may comprise a spatial attention in a direction of an object. The object may be, for example, an object associated with the hazard facing the vehicle, such as a ball in the road, a pedestrian crossing the road, a car running a red light, a curve in the road or another area that is not adequately monitored by the sensors of the vehicle, or the like.

In some exemplary embodiments, the target cognitive state may be a state maximizing the driver's wellbeing and minimizing the potential of risk. For example, the target cognitive state may be determined as the state c that minimizes the following function: $f(c)=\alpha \cdot \text{Risk}(c) - \beta \cdot \text{WellBeing}(c)$. In some exemplary embodiments, WellBeing(c) may be a function of a wellbeing of the human subject given the cognitive state. In some cases, if the driver is unable to engage in desired non-driving tasks, his wellbeing may be reduced. In some exemplary embodiments, the driver wellbeing is assessed utilizing, among others, facial expressions and gestures, pupil dilation, eye saccades, body temperature and other physiological parameters. In some exemplary embodiments, driver profile and history are used for assessing the driver's wellbeing. Additionally or alternatively, the driver's wellbeing may also be affected by non-seamless stimuli that interrupts his activities. In some exemplary embodiments, $\alpha$ and $\beta$ may be coefficients, such as giving relative weights to the Risk and Wellbeing factors. In some exemplary embodiments, the coefficients may be between zero and one and may have a sum of one. In some exemplary embodiments, Risk(c) may be a function of a risk depending on the cognitive state. In some exemplary embodiments, Risk(c) may be a function of an expected damage, given the cognitive state. In some exemplary embodiments, Risk(c) may be defined as Risk(c)=Damage·Probability(c). Damage may be an expected damage from a hazard. Probability(c) may be a function of a probability that the damage will occur, given the cognitive state of the driver.

On Step 240, a saliency level may be determined for a stimuli. In some exemplary embodiments, saliency and content of the stimuli may be determined. In some exemplary embodiments, the saliency and content are compatible with environmental conditions and the urgency level of the situation. In some exemplary embodiments, the saliency of the stimuli may be determined by multiple parameters, including, modality, duration, strength and location. In some exemplary embodiments, the saliency of the stimuli may be gradually increased while monitoring the reaction of the driver until the target cognitive state is reached. In some exemplary embodiments, using this paradigm, the system may operate in a minimally intrusive manner, potentially minimizing a decrease in the wellbeing of the driver.

In some exemplary embodiments, the saliency level for a stimuli may be determined based on the cognitive state, the target state, or the like. In some exemplary embodiments, the saliency level is configured to cause the human subject to direct spatial attention to the stimuli. In some exemplary embodiments, the saliency level is configured to cause the stimuli to be seamless for the human subject given the cognitive state.

In some exemplary embodiments, the modality of the stimuli may be a visual modality. The saliency level may be affected by the location in the field of view of the driver, such as in the focus area, in the near peripheral vision, in far peripheral vision, or the like. Additionally or alternatively, the saliency level may a size of the visual stimuli, an opacity level of the visual stimuli, a brightness level of the visual stimuli, a duration in which the visual stimuli is presented, an angle from the driver's gaze, or the like.

In some exemplary embodiments, the modality of the stimuli may be audio modality. The saliency level may be a volume level of the audio stimuli, a frequency spectrum of the audio stimuli, a similarity measurement of the audio stimuli with respect to a background noise, a duration in which the audio stimuli is provided, or the like. In some exemplary embodiments, there may be a background noise and a pattern that matches the background noise may be used for the audio stimuli. Deviations from the background noise may be noticeable—the greater the dissimilarity, the more salient the stimuli.

In some exemplary embodiments, the saliency level for a stimuli may be determined using a predictive model. In some exemplary embodiments, the predictive model is configured to estimate an estimated saliency level for a stimuli so as to provide a seamless stimuli while directing spatial attention to the stimuli. In some exemplary embodiments, the predictive model provides the estimated saliency level based on the cognitive state, the target cognitive state, or the like. In some exemplary embodiments, the predictive model may be trained based on the driver's response to past stimuli at different cognitive states. Additionally or alternatively, the predictive model may be based on crowd-sourced data, such as of people having similar characteristics as the driver, e.g., similar demographic information, similar sensory perception (e.g., same hearing abilities, similar visual acuity, or the like), similar behavioral patterns, or the like.

In Step 250, a stimuli may be outputted. The stimuli may be outputted using an output module that is suitable for the modality of the stimuli, such as a speaker for an audio stimuli, a display for a visual stimuli, or the like. The output may be provided at the determined saliency level.

On Step 260, a response of the driver may be determined. In some exemplary embodiments, the activity of the driver may be tracked and monitored using sensors. If the driver responds to the stimuli in a conscious or non-conscious manner, the response may be identified.

In some exemplary embodiments, if the stimuli was perceived by the driver in a non-seamless manner (262), the information may be used to update the predictive model for future uses (270). In some exemplary embodiments, the model may be updated in order to reduce the saliency level to avoid non-seamless stimuli in the future. Additionally or alternatively, if there was an effect on the cognitive state of the driver (264), the effect may be analyzed and if it does not match a desired effect, the model may be updated (270). In some exemplary embodiments, if the stimuli did not cause the driver to reach the target cognitive state, the model may be updated accordingly to increase saliency in future attempts. In some cases, a next stimuli at a higher saliency level may then be determined and outputted (e.g., steps 240-270) in order to reach the target cognitive state of Step 230. Additionally or alternatively, the impact of the stimuli to the cognitive state may be determined and the difference between the driver's new cognitive state and the target cognitive state may be identified and used for updating the predictive model.

In some exemplary embodiments, the information collected based on the driver response may be provided to a server for collection. Crowd-sourced data may then be used in an aggregative manner to improve the model for a plurality of drivers using a plurality of vehicles.

In some exemplary embodiments, the predictive model may provide a characteristic of a stimuli which includes a number of different saliency levels in different saliency attributes. Additionally or alternatively, the predictive model may provide the modality of the stimuli. In such embodiments, the modification of the model may cause a future prediction to provide a different stimuli having different characteristics, including some portions that are more salient than before and some portions that are less salient than before. For example, the model may determine a brighter stimuli that is displayed for a shorted time duration. As another example, the model may determine a visual stimuli instead of an audio stimuli.

Figure 3:
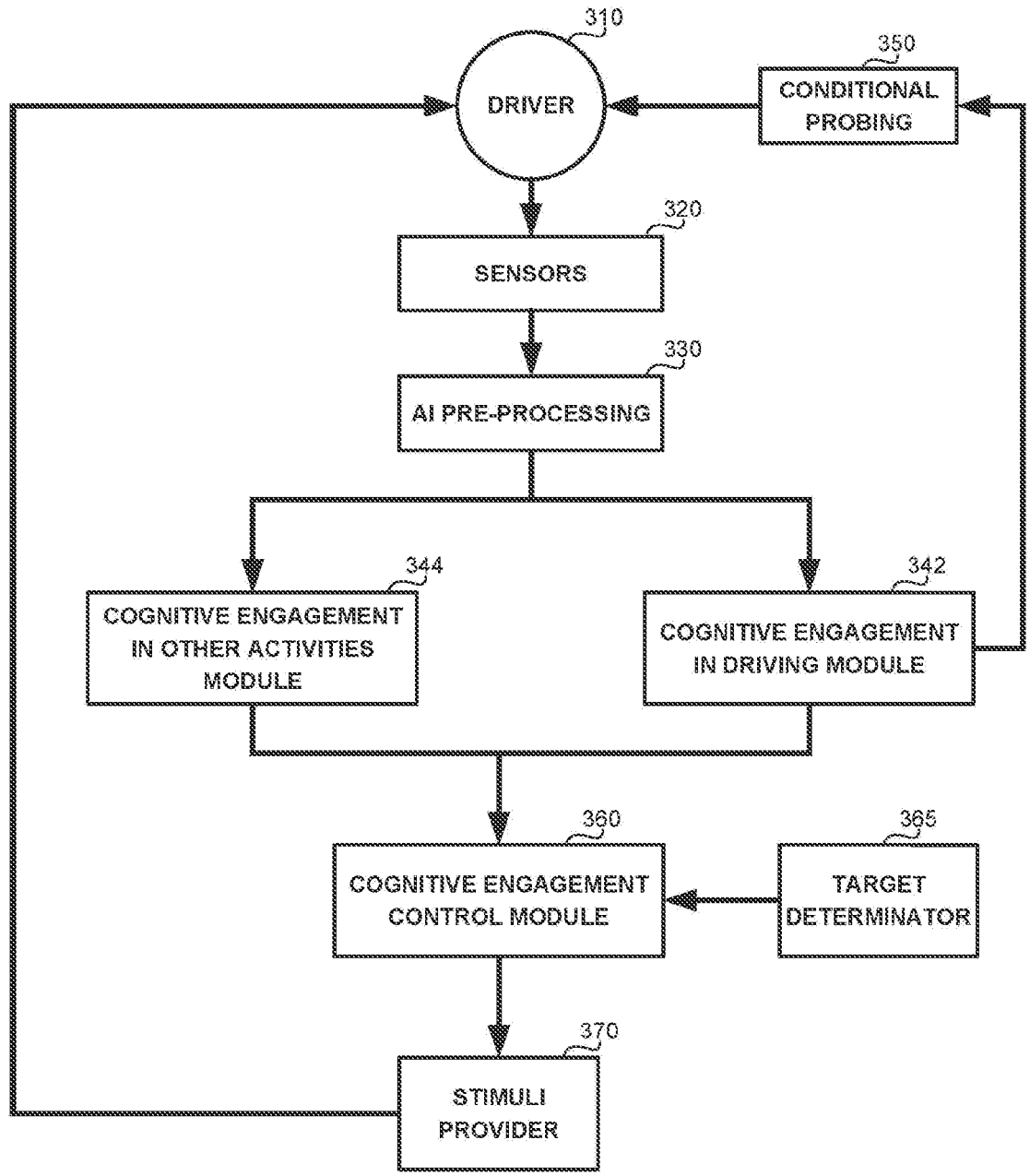
FIG. 3 shows an illustration of system and method, in accordance with some exemplary embodiments of the disclosed subject matter.

Referring now to FIG. 3, showing an illustration of system and method, in accordance with some exemplary embodiments of the disclosed subject matter. The state of Driver 310 is monitored using Sensors 320.

In some exemplary embodiments, an Artificial intelligence (AI) pre-processing 330 may process the data from Sensors 320 to produce second-level features. As an example, AI Pre-Processing 330 may produce a feature relating to gaze direction within the visible scene, a feature relating to pupil dilation, a feature indicative of a behavioral pattern that is indicative of low receptivity levels, or the like. In some exemplary embodiments, the driver wellbeing may be assessed by AI Pre-Processing 330 utilizing, among others, facial expressions and body gestures, pupil dilation, eye saccades, and other physiological parameters. In some exemplary embodiments, driver profile and history are used for assessing the driver's wellbeing. In some embodiments, AI Pre-Processing 330 may utilize a prediction model, such as an Auto-Regressive (AR) model, Kalman filter, particle filter, deep neural networks with Long-Short Term Memory, or the like. The prediction model may be used, for example, to predict any aspect of the cognitive state of the driver, such as but not limited to the focus of the attention of the driver, cognitive engagement of the driver, or the like.

In some exemplary embodiments, the second-level features may be transformed to a vector of receptivity level indicators, together with corresponding confidence level, which may be determined as part of AI Pre-Processing 330. In some exemplary embodiments, if the confidence level is low (e.g., below a threshold), the system may probe Driver 310 by using Conditional Probing 350. Conditional Probing 350 may be operable to produce various stimuli and monitor the reaction of Driver 310 to these stimuli. In view of the driver's response, as measured by Sensors 320 and as processed by AI Pre-Processing 330, a new set of receptivity level indicators may be generated, potentially with higher confidence levels. In some exemplary embodiments, the receptivity level indicators may comprise a feature relating to response to probing, response to specific form of probing, or the like.

In some exemplary embodiments, the receptivity indicators may be fed into a Cognitive Engagement Control Module 360, together with the target cognitive state, determined by Target Determinator 365. Cognitive Engagement Control Module 360 may use these inputs at time T, together with inputs from previous times T−1, T−2, . . . T−N in order to produce a prediction for the cognitive state at T+1. In some exemplary embodiments, the vector of N inputs may be used to produce a control stimuli to be provided to Driver 310 using the Stimuli Provider 370. In some exemplary embodiments, a positive or a negative reward to Driver 310 may be determined and provided using Stimuli Provider 370. In some exemplary embodiments, the reward may be configured to alter the focus of the receptivity of the driver in order of the driver to comply with the situation and to facilitate an adaptive response. In some exemplary embodiments, the reward may be determined so as to improve the quality of the driver's response within the long term. In some embodiments, reinforcement and rewards to Driver 310 include positive and negative reinforcement, operable to condition Driver 310 and to improve the compatibility of the attention, receptivity and engagement to the desired ones. In some embodiments, negative rewards may be induced using low saliency noise and destructions that would make Driver 310 feel slightly uncomfortable when his reaction to the stimuli significantly deviates from an optimal one. In some embodiments, long-term positive rewards include virtual tokens that can be translated to various digital goods or to discounts for shopping or dining, while long-term negative rewards may be obtained by reducing the number of such virtual tokens in the account of Driver 310. In some embodiments, a gamification paradigm is used to provide positive and negative reinforcement as a part of a game. In some embodiments, reinforcement may be coupled with stimuli to create seamless and non-intrusive shaping of the behaviour of Driver 310. This may be used to maintain the receptivity of Driver 310 at a specific level while minimizing unnecessary perceptual load.

In some exemplary embodiments, Stimuli Provider 370 may be operable to display visual stimuli with various levels of saliency. For example, the stimuli may be displayed for a short duration (e.g., 100 milliseconds, 1.5 seconds, or the like) in the peripheral area of the driver visual field. As another example, a barely noticeable audio signal may be provided. The barely noticeable audio signal may be customizable. In some cases, the barely noticeable audio signal may be compatible with the driver's preference and the driver's environment. In some exemplary embodiments, the barely noticeable audio signal may be based on manipulating the environmental sounds detected by system acoustic sensors—e.g., by adding a noise with similar characteristics and modulating the amplitude for short periods while monitoring the driver's reaction. As another example, a tactile module embedded in the driver's seat or steering wheel may be used to introduce tactile stimuli in different levels of magnitude. In some embodiments, the system utilizes subliminal set stimuli that do not increase the cognitive load on the driver, thereby improving the driver's experience.

In some exemplary embodiments, the system may reflect the driver's capacity to handle driving related situation, given the receptivity level assessed by the receptivity level. In some exemplary embodiments, Module 344 may be configured to use sensor data to assess level of engagement in other, non-driving, activities, such as texting, reading, navigating, utilization of the vehicle entertainment and information systems, or the like, together with the corresponding engagement levels. This information may be used as an indication regarding the level of engagement in driving, which may be determined by Cognitive Engagement In Driving Module 342. If the confidence level with respect to the level of engagement in driving is low, Conditional Probing 350 may be utilized. Conditional Probing 350 may be operable to produce various stimuli and monitor the reaction of the driver to these stimuli. Cognitive Engagement Control Module 350 may utilize engagement indicators, together with target cognitive state determined by Target Determinator 365, to determine a stimuli and saliency level thereof.

In some exemplary embodiments, Target Determinator 365 may be configured to determine the target cognitive state, such as a desired engagement level that Driver 310 needs to reach. Target Determinator 365 may determine automatically the target cognitive state, such as based on the current context, current activities, or the like.

Figure 4:
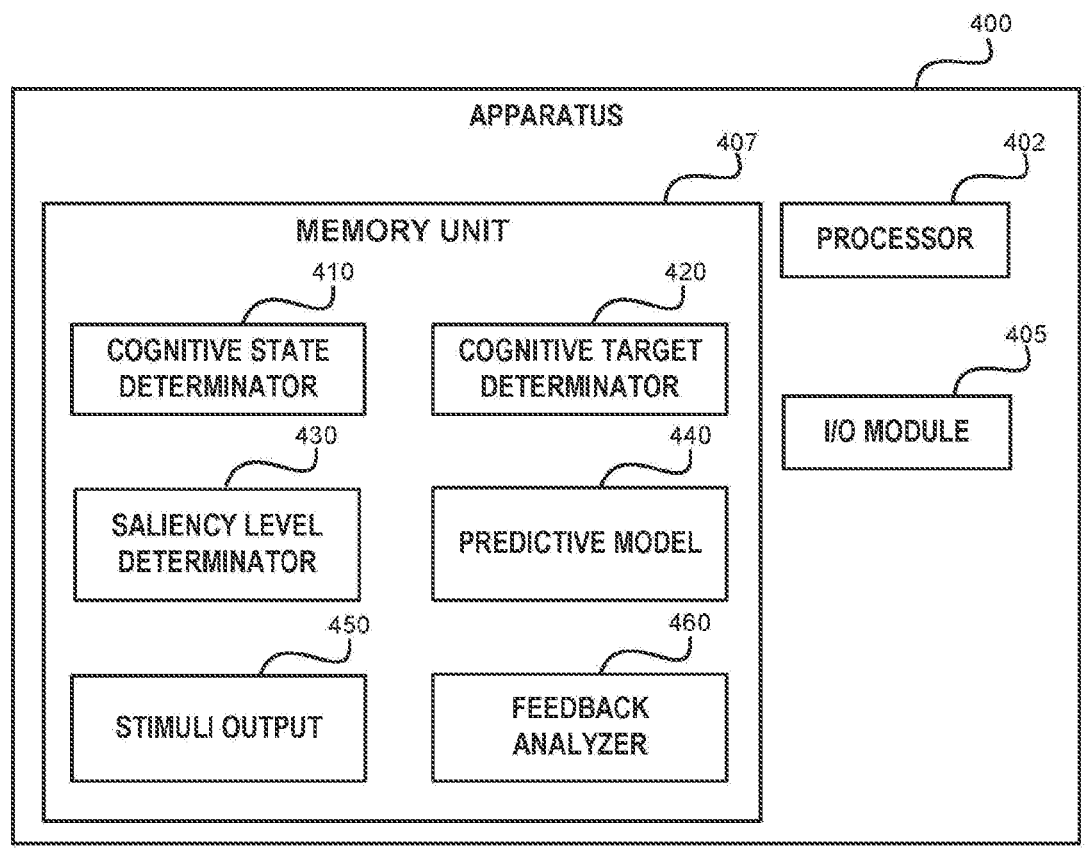
FIG. 4 shows a block diagram of an apparatus, in accordance with some exemplary embodiments of the disclosed subject matter.

Referring now to FIG. 4 showing a block diagram of an apparatus, in accordance with some exemplary embodiments of the disclosed subject matter.

In some exemplary embodiments, Apparatus 400 may comprise one or more Processor(s) 402. Processor 402 may be a Central Processing Unit (CPU), a microprocessor, an electronic circuit, an Integrated Circuit (IC) or the like. Processor 402 may be utilized to perform computations required by Apparatus 400 or any of it subcomponents.

In some exemplary embodiments of the disclosed subject matter, Apparatus 400 may comprise an Input/Output (I/O) module 405. I/O Module 405 may be utilized to provide an output to and receive input. For example I/O Module 405 may be configured to receive sensory information from sensors observing the driver, sensors observing the environment of the vehicle, or the like. Additionally or alternatively, I/O Module 405 may be configured to communicate with external devices, such as connected cars, IoT devices, servers, or the like, enabling transmitting information to and from Apparatus 400.

In some exemplary embodiments, Apparatus 400 may comprise Memory Unit 407. Memory Unit 407 may be a hard disk drive, a Flash disk, a Random Access Memory (RAM), a memory chip, or the like. In some exemplary embodiments, Memory Unit 407 may retain program code operative to cause Processor 402 to perform acts associated with any of the subcomponents of Apparatus 400.

In some exemplary embodiments, Cognitive State Determinator 410 may be configured to determine a cognitive state of the driver. The cognitive state may be determined based on sensor data, based on reference drivers having similar characteristics, or the like. In some exemplary embodiments, Cognitive State Determinator 410 may be configured to determined cognitive engagement in different tasks, such as driving related tasks, non-driving related tasks, or the like. A duration of cognitive engagement for each such task may be determined. In some exemplary embodiments, Cognitive State Determinator 410 may determine cognitive resources of the driver that are free and can be used for cognitive attention associated with driving related tasks.

In some exemplary embodiments, Cognitive Target Determinator 420 may be configured to determine a target cognitive state for the driver. The target cognitive state may be determined based on assed urgency, assed risk level, expected wellbeing of the driver, hazards facing the vehicle, or the like. Additionally or alternatively, the target cognitive state may be determined based on the driver's current cognitive state, as determined by Cognitive State Determinator 410.

In some exemplary embodiments, Saliency Level Determinator 430 may be configured to determine a saliency level for a stimuli, a modality for the stimuli, or the like. The characteristics of the stimuli may be determined so as to have a seamless stimuli provided to driver, given the driver's cognitive state, determined by Cognitive State Determinator 410, and configured to direct the driver's attention towards an object or otherwise divert cognitive attention towards driving related activity. In some exemplary embodiments, stimuli characteristics may be determined so as to cause a change affect the current cognitive state and changing it to become closer towards the target cognitive state, if not identical thereto.

In some exemplary embodiments, Predictive Model 440 may be a model that is used to predict the saliency level and other stimuli characteristic to provide for a seamless stimuli, that effectuates a desired change in the cognitive state of the driver. Model 440 may be trained locally in Apparatus 400, may be received from a server, such as Model Generator and Distributer 110 of FIG. 1, or the like. In some exemplary embodiments, Predictive Model 440 may be determined using training data collected from various drivers and responses to stimuli provided thereto.

In some exemplary embodiments, Stimuli Output 450 may be a module configured to implement the provisioning of the stimuli at a determined modality, having saliency levels as determined by Predictive Model 440, or the like. In some exemplary embodiments, Stimuli Output 450 may be configured to determine a location for stimuli. The location may be determined based on the gaze of the driver, directing his attention relatively to the gaze and focusing the attention on an object. As an example, visual stimuli may be provided in an angle that if the driver shifts his focus to the angle, the driver would view a target object, such as an object associated with a hazard. Additionally or alternatively, using non-balanced audio stimuli, can provide a directional sound. The directional sound may be configured to a relative location that has the same angle as an object of interest from the driver. For example, if the object of interest, such as a pedestrian, is located 110 degrees from the gaze of the driver, the audio stimuli may be provided in a manner simulating a sound being emitted from the location of the object of interest.

Figure 5A:
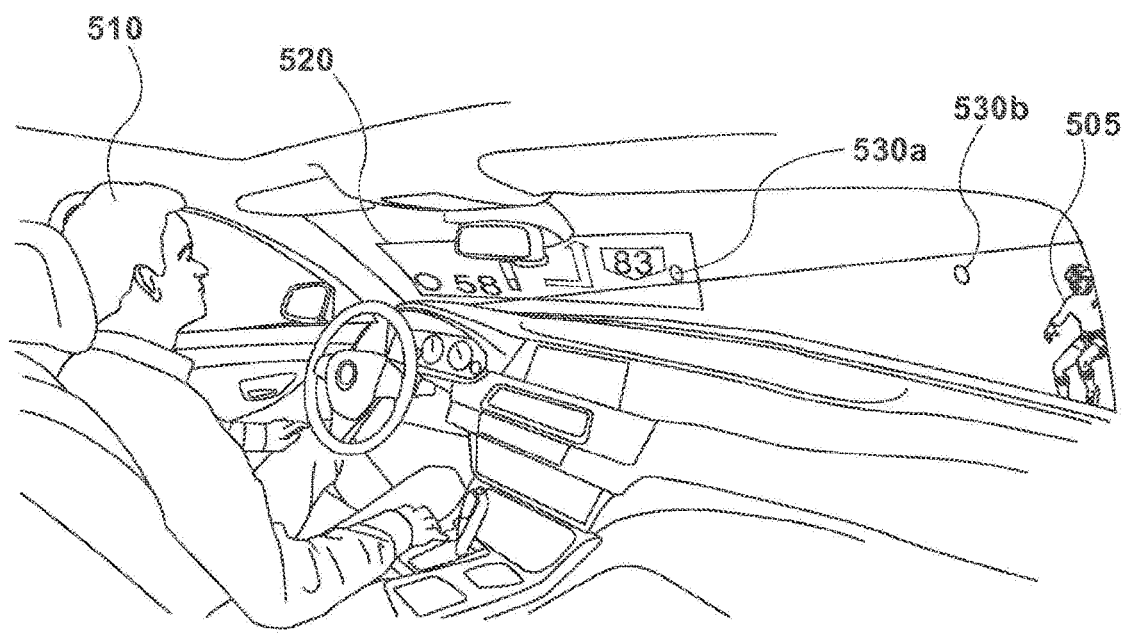
FIGS. 5A-5B show illustrations of visual stimuli, in accordance with the disclosed subject matter.
Figure 5B:
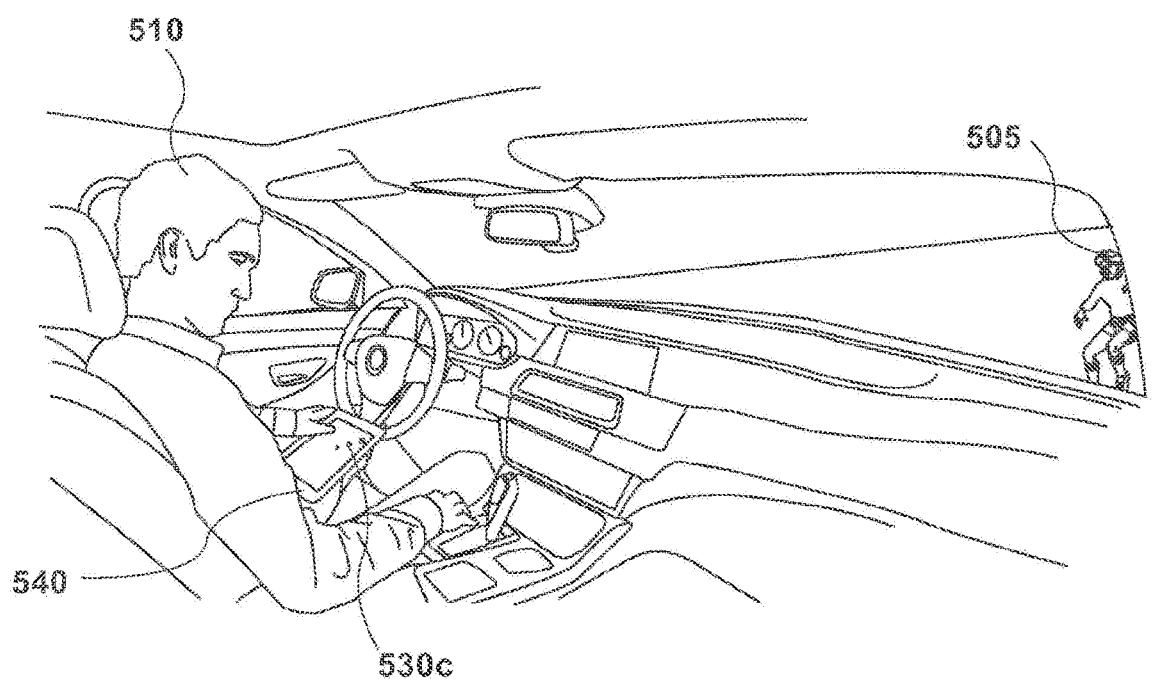

FIGS. 5A-5B show illustrations of visual stimuli, in accordance with the disclosed subject matter.

In FIG. 5A, Driver 510 of a partly autonomous vehicle is directing his attention in a Display 520. Display 520 may be an on-windshield display. Display 520 may be displaying content that is not related to the driving activity, such as a movie, a content of a website, a video conference, or the like. Driver 510 is currently not engaged in driving activity, and the autonomous driver is driving the vehicle.

Pedestrian 505 may be crossing the road, and there is a risk of the vehicle hitting Pedestrian 505. As a result, it may be desired to ensure that Driver 510 is made more alert and capable of reacting, if Driver 510 needs to take over the driving activity to avoid a collision.

As is illustrated by FIG. 5A, Pedestrian 505 is visible outside the windshield. However, the focus of gaze of Driver 510 is at a different location.

In some exemplary embodiments, Stimuli 530a may be visually presented in Display 520 in a location that is relative to both Driver 510 and Pedestrian 505. In some exemplary embodiments, Stimuli 530a is presented in a location that if Driver 510 looks at, Pedestrian 505 is closer to his focus area. In some exemplary embodiments, Stimuli 530a may be presented in a location that is in the peripheral vision of Driver 510. In some exemplary embodiments, Stimuli 530a may be presented using different saliency levels, such as for a limited duration of time, being partly transparent, having limited size, or the like.

Additionally or alternatively, Stimuli 530b is another example of a potential stimuli. As opposed to Stimuli 530a, Stimuli 530b is displayed externally to active display that is being using by Driver 510, Display 520. Stimuli 530b may be presented in a location that is proximate relatively to Pedestrian 505.

In some exemplary embodiments, Stimuli (530a, 530b) may be provided as a seamless stimuli that Driver 510 is not aware of, but affects the cognitive state of Driver 510 so as to improve his ability to react to Pedestrian 505, if he needs to take over the driving activity. The stimuli may be configured to release some cognitive resources from the cognitive engagement the Driver 510 has with respect to Display 520 so as to enable fast and efficient takeover maneuver, if such maneuver would be needed.

In FIG. 5B, Driver 510 is engaged in an activity using a Mobile Device 540. It may be desired to direct the attention of Driver 510 upwards and diagonally so as to raise his focus of gaze to a location where he may be able to view Pedestrian 505. Stimuli 530c may be a pattern of dots that appear sequentially directing his attention in a specific direction. For example, the first dot may be the smallest and each dot may be of an increased size. The last dot may be the dot at the top-right corner of Mobile Device 540. Hence, the size, and the pattern of appearance may instinctively cause a direction of attention in upwards and to the right of Driver 510, such as closer to the location of Pedestrian 505.

In some exemplary embodiments, the disclosed subject matter may be utilized with respect to airplane pilots, and specifically in a configuration where the pilot utilizes the autopilot system for controlling the airplane. In some cases, the pilot's cognitive state may affect her ability to respond to an emergency, to an unexpected event, or the like. Hence, it may be desired to monitor the pilot's cognitive state and utilize seamless stimuli, in accordance with the disclosed subject matter, to direct the pilot's cognitive state to a desired target cognitive state.

It is noted, that although the disclosed subject matter is explained using an embodiment of a partly autonomous car and the driver thereof, the disclosed subject matter is not limited to such embodiment, and may be used in other scenarios where human subject's cognitive state is of interest.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:
   obtaining a cognitive state of a human subject, wherein the cognitive state is determined based on one or more sensors, wherein the one or more sensors monitor the human subject;
   determining, by a processor, a target cognitive state for the human subject, wherein the target cognitive state maximizes a wellbeing of the human subject and minimizes a potential of risk;
   determining, based on the cognitive state and the target cognitive state, a saliency level to be used for generating stimuli, the stimuli comprising a pattern of one or more visual marks that appear in a specific direction, said determining comprising predicting that presenting the stimuli in the saliency level will cause the human subject to direct spatial attention to the specific direction, wherein determining comprising predicting that presenting the stimuli in the saliency level will cause the stimuli to be perceived as seamless for the human subject given the cognitive state; and
   outputting the stimuli at the saliency level to be perceived by the human subject, wherein said outputting is performed by an output module.

2. The method of claim 1, wherein the human subject is a driver of a partly-autonomous vehicle.

3. The method of claim 2, wherein the target cognitive state is associated with a hazard facing the partly-autonomous vehicle.

4. The method of claim 2, wherein said determining the saliency level is performed based on a model, wherein the model is updated based on identified responses of the driver to a plurality of stimuli.

5. The method of claim 2, wherein said determining the saliency level is performed based on the cognitive state of the driver, an assessed risk level and an assessed urgency level.

6. The method of claim 1, wherein the stimuli is supraliminal and above a conscious perception level for the human subject.

7. The method of claim 1, wherein the stimuli is a visual stimuli presented to be perceived by peripheral vision of the human subject.

8. The method of claim 1, wherein the target cognitive state comprises directing the spatial attention of the human subject in the specific direction, the specific direction comprising a direction of an object.

9. The method of claim 8, wherein the pattern of the one or more visual marks appears in a sequential order towards the direction of the object, the stimuli is a visual stimuli that is presented in a field of view of the human subject that is in proximity to the object, with respect to the field of view.

10. The method of claim 1, wherein the saliency level is at least one of the following:
   a size of the one or more visual marks,
   an opacity level of the one or more visual marks,
   a brightness level of the one or more visual marks, and
   a duration in which the one or more visual marks are presented.

11. The method of claim 1, wherein the target cognitive state minimizes a following function: $f(c)=\alpha \cdot Risk(c) - \beta \cdot WellBeing(c)$, wherein c is a cognitive state, wherein Risk(c) is a function of a risk depending on the cognitive state, wherein WellBeing(c) is a function of a well being of the human subject given the cognitive state, wherein $\alpha$ and $\beta$ are coefficients.

12. The method of claim 11, wherein Risk(c) is a function of an expected damage that is defined as $Risk(c) = Damage \cdot Probability(c)$, where Damage is an expected damage from a hazard, wherein Probability(c) is a function of a probability that the damage will occur, given the cognitive state of the human subject.

13. The method of claim 1, wherein said determining the saliency level is based on a wellbeing of the human subject, wherein the wellbeing of the human subject is assessed using at least one of the following:
   a facial expression of the human subject;
   eye saccades of the human subject;
   one or more body gestures of the human subject; and
   one or more changes in body temperature of the human subject.

14. The method of claim 1, wherein said determining the saliency level is performed using a predictive model, wherein the predictive model is configured to determine an estimated saliency level for generating the stimuli that is predicted to provide a seamless stimuli while directing the spatial attention of the human subject to the stimuli, wherein the predictive model provides the estimated saliency level based on the cognitive state, the target cognitive state and a characteristic of the human subject.

15. The method of claim 13, wherein the predictive model is trained based on crowd-sourced information relating to different people driving different vehicles.

16. The method of claim 1,
   wherein said determining the saliency level is performed based on a predictive model;
   wherein said method further comprising:
      identifying a response of the human subject to the stimuli; and
      updating the predictive model, whereby improving determinations of saliency levels in future usages of the predictive model.

17. The method of claim 16, wherein said identifying the response comprises obtaining a new cognitive state of the human subject in response to said outputting, wherein said updating the predictive model is based on a difference between the new cognitive state and the target cognitive state, wherein the response is indicative that the stimuli was not perceived as seamless to the human subject, wherein the method comprises updating, based on the response, the predictive model to provide a lower saliency level than the saliency level determined in said determining the saliency level for a same condition.

18. The method of claim 16, wherein said identifying the response comprises obtaining a new cognitive state of the human subject in response to said outputting, wherein said updating the predictive model is based on a difference between the new cognitive state and the target cognitive state, wherein the response is indicative that the stimuli did not cause the human subject to direct spatial attention to the stimuli, wherein the method comprises updating, based on the response, the predictive model to provide a higher saliency level than the saliency level determined in said determining the saliency level for a same condition.

19. An apparatus comprising a processor and coupled memory, the processor being adapted to perform:
   obtaining, by the processor, a predictive model, wherein the predictive model is trained on crowd-sourced responses of different drivers to different stimuli with various saliency levels, wherein the predictive model is configured to determine, based on a given cognitive state and a given target cognitive state, a desired saliency level for given stimuli, the desired saliency level is predicted to be required for ensuring that the given stimuli will be perceived as seamless to the driver and that spatial attention of the driver will be directed to the given stimuli;
   obtaining, by the processor, a cognitive state of a human subject, wherein the cognitive state is determined based on one or more sensors, wherein the one or more sensors monitor the human subject;
   determining, by the processor, a target cognitive state for the human subject, wherein the target cognitive state maximizes a wellbeing of the human subject and minimizes a potential of risk;
   using the predictive model to determine, based on the cognitive state and the target cognitive state, a saliency level to be used for generating stimuli, wherein outputting the stimuli at the saliency level is predicted, by the predictive model, to cause the human subject to direct spatial attention to the stimuli, wherein outputting the stimuli at the saliency level is predicted, by the predictive model, to cause the stimuli to be perceived as seamless for the human subject; and
   outputting the stimuli at the saliency level to be perceived by the human subject, wherein said outputting is performed by an output module.

20. The apparatus of claim 19, wherein the target cognitive state comprises directing the spatial attention of the human subject in a specific direction, the specific direction comprising a direction towards a location of an object, wherein the stimuli is an audio stimuli that is configured to be perceived by the human subject with an associated relative location, wherein the relative location is relative to the human subject and corresponds the location of the object.

21. The apparatus of claim 19, wherein the stimuli is an audio stimuli, wherein the saliency level is at least one of the following:
a volume level of the audio stimuli,
a frequency spectrum of the audio stimuli,
a similarity measurement of the audio stimuli with respect to a background noise, and
a duration in which the audio stimuli is provided.

22. The apparatus of claim 19, wherein the predictive model comprises a deep learning model that is trained using reinforcement learning, wherein a training dataset of the predictive model is absence of past information relating to the human subject.

23. A non-transitory computer readable medium retaining program instructions, which program instructions when read by a processor, cause the processor to perform:
obtaining a cognitive state of a human subject, wherein the cognitive state is determined based on one or more sensors, wherein the one or more sensors monitor the human subject;
determining, by the processor, a target cognitive state for the human subject, wherein the target cognitive state maximizes a wellbeing of the human subject and minimizes a potential of risk;
determining, based on the cognitive state and the target cognitive state, a saliency level to be used for generating stimuli, the stimuli comprising a pattern of one or more visual marks that appear in a specific direction, said determining comprising predicting that presenting the stimuli in the saliency level will cause the human subject to direct spatial attention to the specific direction, wherein said determining comprising predicting that presenting the stimuli in the saliency level will cause the stimuli to be perceived as seamless for the human subject given the cognitive state; and
outputting the stimuli at the saliency level to be perceived by the human subject, wherein said outputting is performed by an output module.

* * * * *